United States Patent [19]

Van Steenwyk et al.

[11] 4,173,228
[45] Nov. 6, 1979

[54] CATHETER LOCATING DEVICE

[75] Inventors: Donald H. Van Steenwyk, San Marino; Ira N. Childress, Los Angeles, both of Calif.

[73] Assignee: Applied Medical Devices, San Marino, Calif.

[21] Appl. No.: 797,318

[22] Filed: May 16, 1977

[51] Int. Cl.² .................................................. A61M 25/00
[52] U.S. Cl. .................................... 128/653; 128/349 R
[58] Field of Search ................. 128/1.3, 1.4, 1.5, 2 R, 128/2 M, 2 S, 2.05 R, 2.05 E, 348–351, 4–8

[56] References Cited

U.S. PATENT DOCUMENTS

| | | | |
|---|---|---|---|
| 2,949,910 | 8/1960 | Brown et al. | 128/2 R |
| 3,043,309 | 7/1962 | McCarthy | 128/348 |
| 3,253,588 | 5/1966 | Vuilleumier et al. | 128/2 R |
| 3,661,148 | 5/1972 | Kolin | 128/2 S |
| 3,847,157 | 11/1974 | Caillouette et al. | 128/2 M X |

FOREIGN PATENT DOCUMENTS 2432173  1/1976  Fed. Rep. of Germany .......... 128/2 M

*Primary Examiner*—Dalton L. Truluck
*Attorney, Agent, or Firm*—Christie, Parker & Hale

[57] ABSTRACT

A system for detecting and monitoring the position of a catheter tip during insertion and after placement of the catheter in a body cavity. A coupling means such as an inductor coil is secured adjacent the catheter tip, and leads extend from the coil along the catheter for connection to external indicating equipment. Energy is propagated through the body to the coupling means from an external source such as an oscillator-driven coil or coils, and relative proximity and orientation of the external and catheter coils is determined by monitoring amplitude and phase of the signal induced in the catheter coil.

15 Claims, 9 Drawing Figures

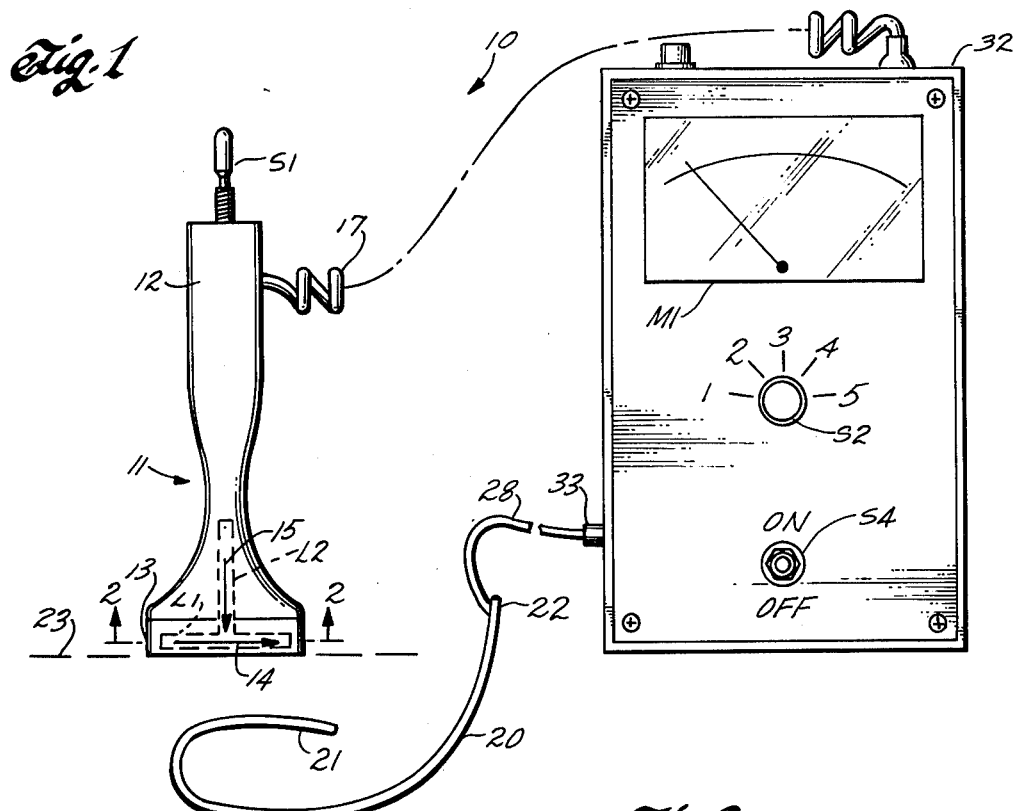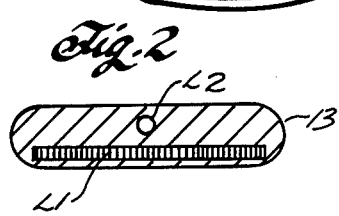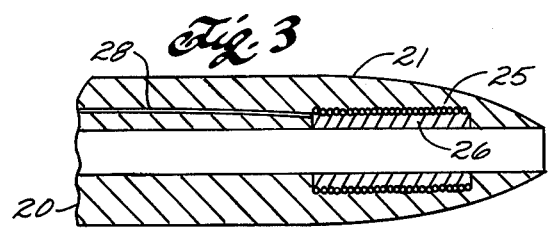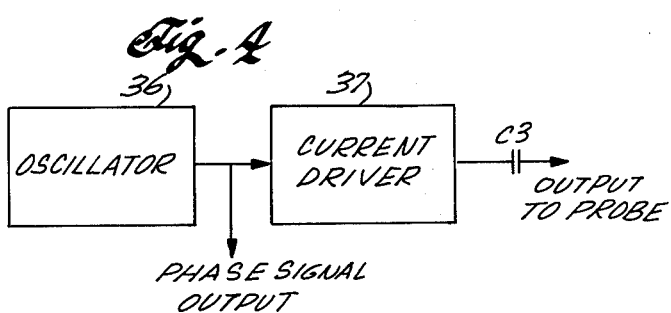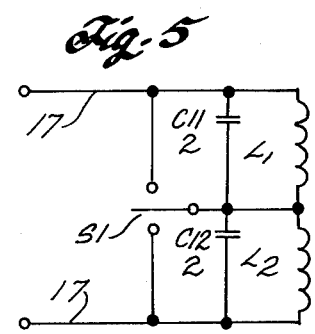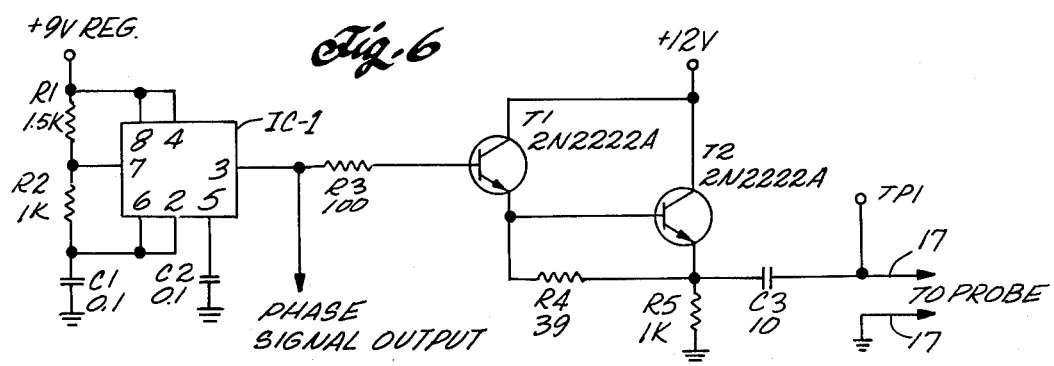

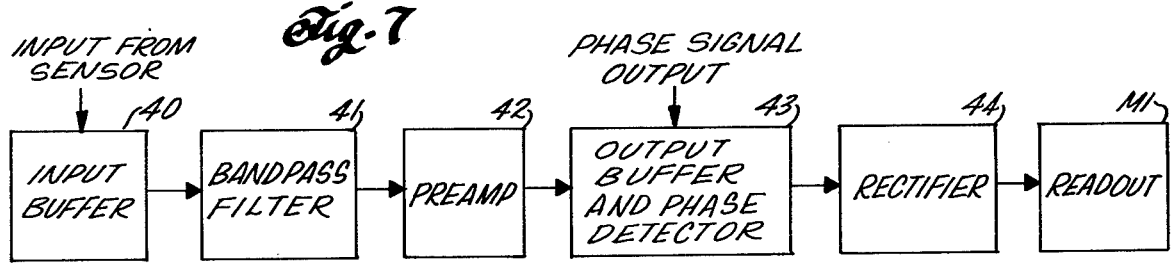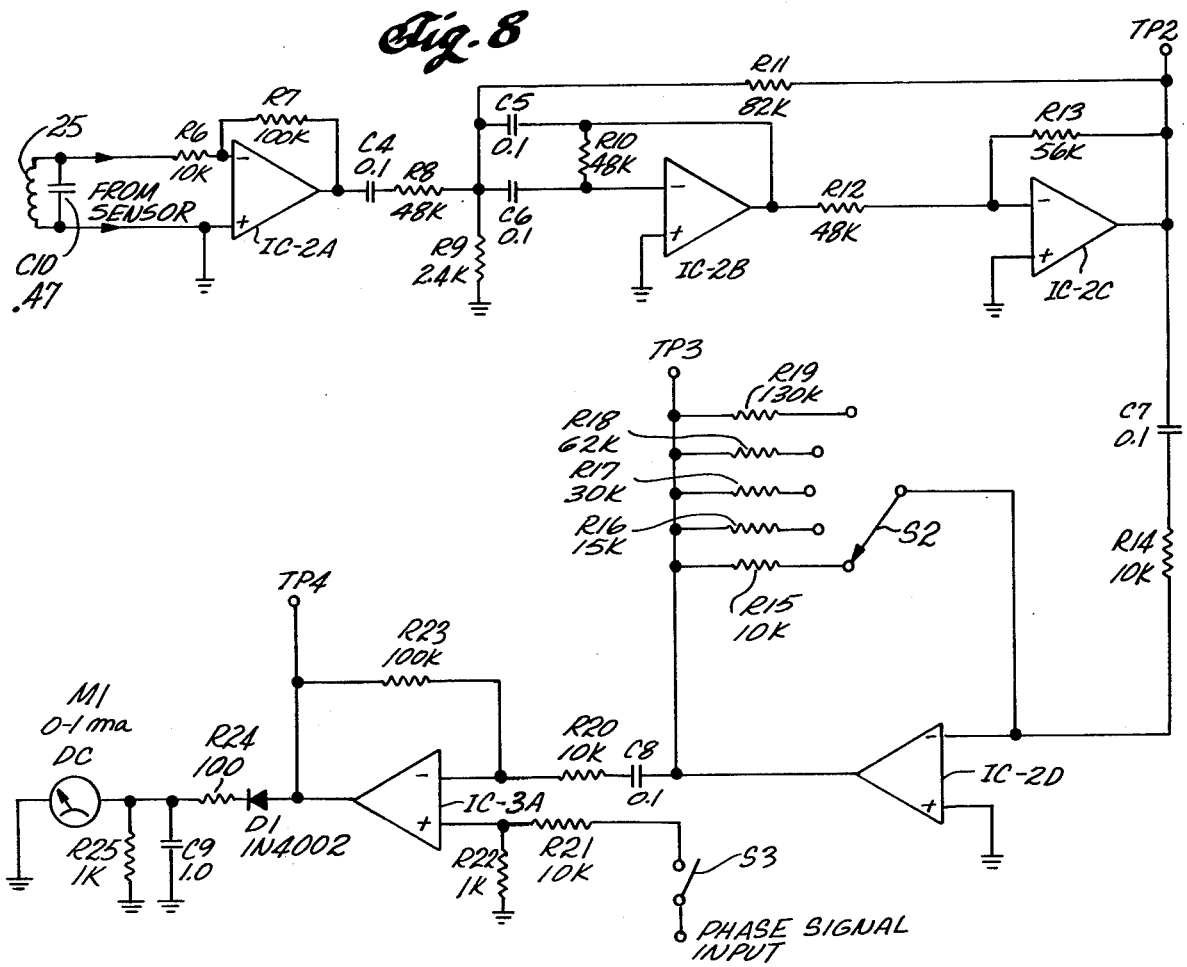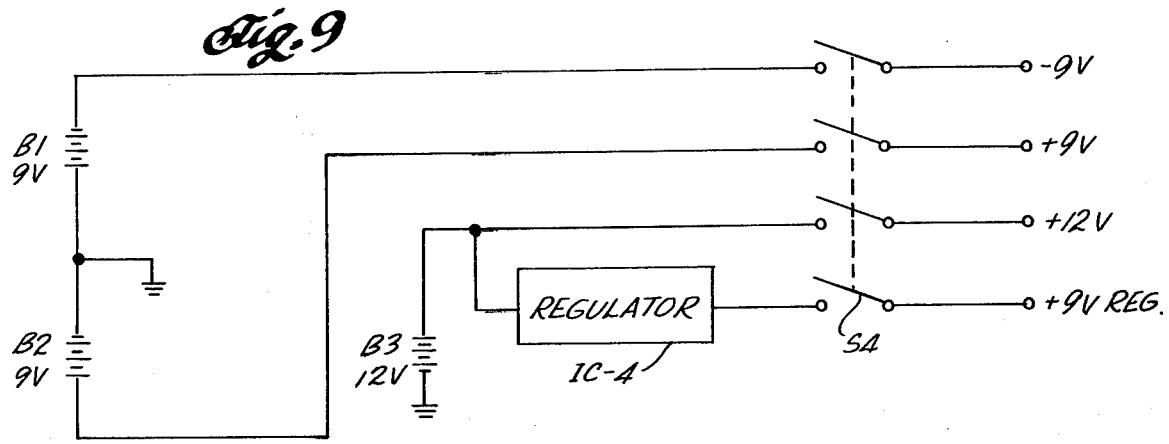

CATHETER LOCATING DEVICE

BACKGROUND OF THE INVENTION

There are a variety of medical procedures which involve insertion of a catheter or slender tube into a body cavity or passage. The term "catheter" is used herein to describe all such devices, whether they be for probing a body passage, delivering or extracting a fluid, or for transporting an apparatus or instrument to a point within the body where a function is to be performed. "Catheter" thus means any invasive device, whether solid or hollow, which is intended for insertion in a body orifice or into an internal duct or passage through an external incision.

For example, catheterization may be needed in diagnosis and treatment of illnesses involving the brain, heart, lungs, bladder, etc. After the catheter is placed, it may be used to introduce or withdraw fluids from the cavity being probed, or it may be used as a carrier to support an instrument for measuring pressure or performing some other function in the cavity.

The catheter is inserted through an incision, or through the mouth or other body orifice, and is fed along an internal passage leading to the body area of interest. It is important to monitor the position of the catheter tip during insertion, because it is sometimes possible for the tip to be guided into the wrong passage at, for example, a Y-shaped junction of blood vessels or the like. Similarly, it is sometimes important to monitor the position of a catheter placed for long-term use to insure that the catheter has not moved within the body.

One catheter-locating technique which is well known in medicine involves coating, impregnating or otherwise positioning a radiopaque material on the catheter or at least the distal end portion of the catheter. The catheter position can then be determined by conventional X-ray procedures. This technique, however, requires expensive and bulky equipment operated by trained personnel, and involves a normally undesirable irradiation of the body with X-rays. The technique is also relatively slow, and can significantly extend the time required for catheter insertion which may require repeated monitoring of tip position as the catheter is moved toward the target position.

A more recent technique for catheter position monitoring is described in U.S. Pat. No. 3,847,157—Caillouette and Johnson disclosing a catheter which carries a magnetic material. Catheter position is monitored with a movable external magnetic-field sensor which indicates proximity to the catheter magnetic material. This arrangement appears satisfactory in many applications, but may not provide a clear position indication of a deeply implanted catheter, and is also susceptible to interference from stray or ambient magnetic fields.

The catheter position monitor of this invention uses a catheter with a coupling or field sensing device at the catheter distal tip, the device having connecting wires extending back through the catheter tube to an amplifying and detecting circuit external to the body. An external transmitter is positioned to generate an energy field which penetrates the body and is sensed by the device at the catheter tip. The relatively weak signal received from the device is externally processed to provide amplitude and phase information which enables determination of the position and orientation of the catheter tip.

The invention permits use of a strong and deeply penetrating energy field because the field generator is external and not subject to the size and electrical limitations which characterize implantable devices. Connection of the sensor to external equipment enables amplification of weak signals to a level convenient for further processing and display. The hazards, inconvenience and expense of X-ray position monitoring are avoided, and catheter position is quickly and easily determined both during insertion and after placement of the catheter.

SUMMARY OF THE INVENTION

This invention relates to a system for determining the position of a medical catheter having a distal tip or first end inserted in a body passage, and a second end which remains external to the body. A receiver coupling means having at least two terminals is mounted on the catheter adjacent the first end, and is adapted to generate a signal between the terminals responsive to externally generated energy which is propagated into the body. The receiver coupling means has a connection means connected to the terminals and extending therefrom along the catheter toward the second end to be accessible outside the body. In a presently preferred form, the receiver coupling means is an inductive coil in the catheter wall adjacent the distal tip.

External equipment for the system includes a generating means for propagating energy in wireless fashion to the receiver coupling means, and preferably the generating means is an oscillator which drives an inductive coil to propagate an electromagnetic field into the body. An external amplifier is coupled to the connection means to receive the signal from the receiver coupling means, and the amplifier drives a display or readout device which indicates the extent of coupling of energy between the generating means and receiver coupling means, and thereby to indicate the position and orientation of the catheter distal tip within the body. The coils and amplifier are tuned to the operating frequency to maximize energy coupling through the body, and to minimize interference from stray fields which may be radiated from other equipment.

BRIEF DESCRIPTION OF THE DRAWINGS

FIG. 1 is an elevation of components of a catheter locating system according to the invention;

FIG. 2 is a sectional view on line 2—2 of FIG. 1;

FIG. 3 is an enlarged sectional view of the distal tip of a catheter modified in accordance with the invention;

FIG. 4 is a block diagram of an oscillator circuit;

FIG. 5 is a schematic diagram of probe coils and associated switching used in the invention;

FIG. 6 is a detailed wiring diagram of the oscillator circuit shown in FIG. 4;

FIG. 7 is a block diagram of a receiver circuit;

FIG. 8 is a detailed wiring diagram of the receiver circuit shown in FIG. 7; and FIG. 9 is a wiring diagram of a power supply for the system.

DESCRIPTION OF THE PREFERRED EMBODIMENT

FIG. 1 shows a catheter locating system 10 which includes a hand-held search probe 11 having a handle portion 12 and an enlarged base 13. A pair of inductive coils L1 and L2 are mounted in the probe base. Coil L1 is parallel to and immediately adjacent the lower edge of the probe base, and coil L2 is perpendicularly oriented to coil L1 and has a lower end terminating immediately adjacent the midpoint of coil L1, as shown in FIG. 2. A pair of mutually perpendicular orienting arrows 14 and 15 are marked on the side of the probe base to indicate the positions of the axes of the two coils.

A coil selector switch S1 is positioned at one end of handle portion 12, and a connecting cable 17 extends from the probe. The probe handle and base are preferably made of plastic or a similar material which will not shield or otherwise interfere with the field generated by the coils.

Coils L1 and L2 are selected according to the desired operating frequency, and in a typical arrangement using a frequency of 500 Hz, each coil consists of about 1,000 turns of #34 AWG copper wire wound on a ferromagnetic core about 0.25 inch in diameter and 1.5 inch in length. The individual coils are typically connected in a series configuration (FIG. 5) and are selectively or simultaneously energized as part of the catheter location procedure. Other coil configurations can also be selected. The series connection of the two coils is in turn connected to the arm of switch S1 which is a three-position (center off) SPDT switch, the contacts of which are connected to opposite ends of the two coils. The series-connected coils terminate in two leads which make up connecting cable 17, and a pair of capacitors C11 and C12 are connected across the respective coils.

A typical catheter 20 is shown in FIG. 1, and the catheter has a distal end or tip 21 configured for insertion in the body. A second end 22 of the catheter remains external to the body. A dashed line 23 in FIG. 1 simulates the body surface through which the catheter is inserted.

The distal tip of the catheter is shown in greater detail in FIG. 3, and the tip includes a receiver coupling means such as a coil 25. The coil includes a magnetic core 26 which is embedded in the inner wall of the catheter tip. Preferably, the core is made of a material such as type 410 magnetic stainless steel which is compatible with the requirements of body-invasive devices. The coil is wound on the core, and is typically a multi-layer wrapping of 500 to 1,000 turns of #51 AWG copper wire tuned to match the probe coils.

A two-conductor cable 28 is electrically connected to the two terminals or ends of the coil, and the cable extends rearwardly along the wall of the catheter to emerge adjacent second end 22 as shown in FIG. 1. The cable may extend through the catheter bore, but is preferably embedded in the tube sidewall to be isolated from fluids which may flow through the catheter. Catheters with sidewall-embedded electrical cables are known and commercially available for use with other kinds of devices positioned at a catheter tip.

The circuitry and a battery power supply for the catheter locating system is conveniently mounted in a housing 32 (FIG. 1) to which connecting cable 17 is attached. Cable 28 from the catheter tip is also coupled to the housing by a removable connector 33. The front panel of the housing includes a meter M1, a range selector switch S2, and a power switch S4.

The circuitry associated with the coils in the search probe is shown in block diagram in FIG. 4, and includes an oscillator 36, the output of which is fed to a current driver 37. The output of the current driver is in turn connected through a capacitor C3 to the probe coils.

The circuitry for the coil-driving equipment is shown in detail in FIG. 6. An integrated circuit IC-1 forms the heart of the oscillator circuit, and may be of a conventional type such as a Signetics Type 555. The frequency of the oscillator output signal is controlled by resistors R1 and R2, and capacitor C1, and typical component values for a 500-Hz output signal are shown in the schematic.

The current driver includes an input resistor R3, and two transistors T1 and T2 coupled as a Darlington pair, the output of which is fed through a capacitor C3 to the probe coils. Resistor R4 prevents thermal runaway and transistor damage if the probe-coil connections are short-circuited, and resistor R5 establishes proper transistor biasing for a no-load condition. Capacitors C11 and C12 are selected for maximum developed voltage across probe coils L1 and L2 respectively. Circuit values for a typical configuration are indicated on the drawing, with resistance values being indicated in ohms and capacitor values in microfarads.

The receiver circuitry for processing an input signal from the catheter coil is shown in block-diagram form in FIG. 7. The circuitry includes an input buffer 40 connected to a bandpass filter 41 and preamplifier 42 which drives an output buffer and phase detector 43. The output of circuit 43 is fed through a rectifier 44 to a readout device such as meter M1. The receiver circuitry is shown in detail in FIG. 8 which again indicates typical circuit values with resistance shown in ohms and capacitance shown in microfarads. The amplifiers designated as IC-2A through 2D and IC-3A are preferably integrated-circuit amplifiers such as National Semiconductor Corporation Type LM324.

Amplifier IC-2A and capacitor C4 comprise the input buffer which isolates the receiver or sensor coil from the bandpass filter. Capacitor C10 is selected to optimize sensor coil sensitivity. The input buffer typically has a gain of about ten as determined by resistors R6 and R7. The bandpass filter includes amplifiers IC-2B and IC-2C, the output of which is coupled through capacitor C7 to a range-selecting amplifier IC-2D, the gain of which is determined by resistor R14 and one of resistors R15-19 as selected by switch S2.

The output of the range-selecting circuit is coupled through capacitor C8 to output buffer amplifier IC-3A which in turn drives meter M1 through a rectifier circuit comprising diode D1, capacitor C9, and resistors R24 and 25. Output buffer amplifier IC-3A also receives an input through SPST switch S3 and resistor R21 which are series connected to the output of integrated circuit IC-1 in the probe-coil oscillator as shown in FIG. 6, enabling meter M1 to indicate whether the two resulting input signals to amplifier IC-3A are in phase or out of phase.

A simple battery power supply for the circuit is shown in FIG. 9, and the circuit includes an integrated-circuit voltage regulator IC-4 to provide the regulated voltage output shown on the drawing. A voltage regulator such as a National Semiconductor Corporation Type LM3910 is satisfactory for the circuit. The power supply circuit includes a four-section on-off switch S4 which is mounted on the front panel of housing 32.

The probe-coil oscillator is peaked by connecting the oscillator to the coils L1 and L2 and selecting capacitors C11 and C12 (FIG. 5) to maximize the rms voltage at test point TP1 (FIG. 6). Capacitors C5 and C6 of the bandpass filter (FIG. 8) re selected to tune the filter to the operating frequency of the transmitter. Resistors R10-13 and capacitors C5-6 determine the bandwidth and gain of the filter, and typical values are shown in FIG. 8. The range-selecting circuit values are typically selected by aligning the catheter and probe coils side by side with about one-inch separation, and selecting resistor R19 to produce about one volt rms at test point TP3 (FIG. 8). The catheter and probe coils are then separated to reduce the voltage at test point TP3 to about 0.1 volt rms, and R18 is selected to restore the voltage at test point TP3 to one volt. This step is repeated to establish the values of R17, R16 and R15.

The catheter and probe coils are next restored to the original separation of about one inch, and resistor R24 is chosen to produce a full-scale reading on meter M1. The catheter and probe coils are then widely separated, and resistor R21 is selected (after closing switch S3) to produce a one-half of full-scale reading on the meter.

The catheter locating system operates on the basis of mutual inductive coupling between the probe and catheter coils. The electromagnetic field generated by the probe coil or coils radiates through the body and a voltage is induced in the catheter coil and sensed by the receiver circuit. The magnitude and phase of the induced signal are related to field strength, separation of the coils, and relative orientation of the probe and catheter coils.

The induced signal is maximized when the axes of the probe and catheter coils are parallel and the coils are laterally or axially aligned. The signal is minimized when one coil axis is rotated 90° from the position just described to be perpendicular to the other coil axis. The relative phase of the transmitted and received signals indicates whether the coils are facing in the same or opposite directions, and thus determines the direction in which the catheter distal tip is pointing.

In use, the catheter is inserted in the body to a point where the doctor feels that actual internal position should be verified. The probe is then moved over the assumed position of the distal tip, with the flat base of the probe against or at least parallel to the skin. The probe is then moved both parallel and perpendicular to the long axis (indicated by arrow 14) of the probe base, and the probe is rotated about the long axis of its handle.

This initial scan is made with switch S1 positioned to short coil L2 so only coil L1 generates a field. The linear and rotational movement is continued until a maximum receiver signal is shown on meter M1. Range switch S2 is adjusted to provide reasonable meter deflection without pegging the needle. When the probe position for maximum induced signal is achieved, the position of the center of the probe base is marked on the patient's skin, and a line is drawn through this first mark to show the orientation of the long axis of the probe base.

Switch S1 is then repositioned to short coil L1 so only coil L2 generates a field. With the probe positioned in the same location which produced the maximum signal in the first scan, the reading of meter M1 is noted. If no significant signal is shown, the catheter-tip position determined in the first scan is accurate, and the center of the catheter coil is directly below the first mark with the catheter tip pointing in the direction of arrow 14. Depth of the catheter tip is estimated from the magnitude of the received signal as shown by the meter reading and the setting of the range-selector switch.

If a significant signal is noted during the test described in the last paragraph, a second scan is made along the long axis of the probe base to determine a new position of maximum coupling as indicated by a peak in the meter reading. A slight lateral movement of the probe base is also made to insure that the maximum peak reading is achieved. The position of the center of the probe base is then marked on the skin, and the catheter tip is now known to be beneath a line connecting the first and second marks.

Switch S1 is then placed in the "center off" position to energize both probe coils, and the probe base is moved along the line connecting the first and second marks with arrow 14 pointing toward the second mark. As the probe is moved from the first mark toward the second mark, a dip or peak will be noted in the induced signal reflected by the reading of meter M1. The catheter coil is directly under the center of the probe base when the dip or peak occurs. A dip in signal strength shows that the catheter distal tip is pointing away from the probe base, and a peak shows the tip is pointing toward the probe base.

This procedure can be repeated as many times as necessary during catheter insertion to insure that the catheter tip is following a desired path. The tip position of a fully inserted catheter can also be checked periodically to insure that the tip has not drifted to a new location. Similarly, tip position may be constantly monitored if desired by taping one or more transmission coils to the patient's skin directly over the catheter coil, and then noting any change in meter reading with time.

A relatively low operating frequency of say a few hundred to about twenty thousand Hertz is generally preferred for the catheter locating system because electromagnetic energy in this frequency range propagates through the body but does not interfere with other electronic equipment which may be in use adjacent the patient. The concept of the invention, however, is not restricted to any specific frequency range or type of energy field. For example, a magnetic field may be externally generated, and sensed by a device (such as a Hall-effect transducer or a yttrium-iron-garnet oscillator) at the catheter tip and wired to an external amplifier and display device. Similarly, sonic energy can be propagated through the body to be sensed by an acoustic transducer at the catheter tip and wired to external equipment.

A variety of "antenna" arrays are also suitable for propagating energy into the body for detection by a sensor at the catheter tip and wired to external readout devices. For example, a single inductive coil may be used in the probe, and ambiguities in the direction of the catheter tip are resolved by use of the phase-comparison circuit already described. Three or more coils may also be used in an array, and the coils can be driven with different frequencies for external discrimination to enable a more rapid determination of catheter tip position. This concept can be extended to a multiplicity of fixed-position multiplexed "transmitter" coils which cooperate with sophisticated external detection and display equipment connected to a transducer or field-coupling device at the catheter tip.

There has been described a catheter locating system which avoids the problems associated with prior-art X-ray techniques, and which enables medical personnel to make a quick and accurate determination of catheter tip position as often as needed during installation or placement of the catheter. The equipment used in the system is relatively simple and inexpensive, and is easily used without extensive training. The energy fields propagated into the body are in a frequency range which is unlikely to interfere with other medical equipment, and current levels in the catheter leads are very low (typically pico-amperes) to insure compatibility with legal and ethical considerations of patient safety.

What is claimed is:

1. A locating system for determining the position of a medical catheter inserted in a body, comprising:
   an elongated catheter having a first end adapted for insertion in the body, and a second end which remains external to the body during insertion and use of the catheter;
   a receiver coupling means mounted on the catheter adjacent the first end, the receiver coupling means having at least two terminals and being adapted to receive energy radiated from a remote source, and to generate a signal between the terminals which is analogous to the received energy;
   connection means connected to the terminals of the receiver coupling means and extending along the catheter toward the second end to terminate outside the body;
   generating means external to the body for generating a body-penetrating energy field detectable by the receiver coupling means; and
   indicating means connected to the connection means for displaying the extent of coupling between the generating means and receiver coupling means, and thereby indicating the position of the catheter first end within the body.

2. The system defined in claim 1 wherein the generating means generates an alternating field of a known frequency, and wherein the indicating means includes filter means tuned to reject frequencies differing substantially from said known frequency.

3. The system defined in claim 2 wherein the alternating field is an electromagnetic field.

4. The system defined in claim 3 wherein the receiver coupling means comprises an inductive coil.

5. The system defined in claim 4 wherein the coil includes a core of magnetic material, the core being secured to the catheter.

6. The system defined in claim 5 wherein the coil core is magnetic stainless steel.

7. The system defined in claim 3 wherein the generating means comprises an oscillator, and a first inductive coil coupled to the oscillator to generate the electromagnetic field.

8. The system defined in claim 7 wherein the frequency of the oscillator and electromagnetic field is in the range of about 200 to 20,000 Hertz.

9. The system defined in claim 7 wherein the indicating means includes a phase-sensitive circuit coupled to the oscillator for comparing the relative phase of the oscillator frequency and the frequency of the signal induced in the catheter coil.

10. The system defined in claim 7 wherein the inductive coil of the generating means is mounted in a hand-held probe adapted to be movable with respect to the body.

11. The system defined in claim 7 wherein the generating means further comprises a second inductive coil transversely oriented with respect to the first inductive coil and adapted for connection to the oscillator.

12. The system defined in claim 11, and further comprising switching means interconnecting the oscillator and first and second coils, and enabling selective excitation of the individual coils and alternatively of both coils simultaneously.

13. The system defined in claim 7 wherein the indicating means includes a meter or other means for displaying the magnitude of the signal received from the catheter coil, and a range-changing circuit either automatic or manual for adapting the meter to accommodate catheter-coil signals of significantly different magnitudes.

14. A method for determining the position of a catheter tip inserted in a living body, comprising the steps of:
   inserting the catheter tip into the body, the tip having a coupling means thereon for generating a signal responsive to an energy field, the coupling means having connections extending to an external end of the catheter for connection to an external indicating means;
   irradiating the body with an energy field which is propagated in wireless fashion into the body to the catheter-tip coupling means, the energy field being emitted from a source external and movable with respect to the body; and
   determining the extent of coupling of the coupling means by monitoring the indicating means as the external source is moved to derive information on the position of the catheter tip.

15. The method defined in claim 14, wherein the energy field is an electromagnetic field propagated from an oscillator-driven inductive coil.

* * * * *